(12) United States Patent
Nakanishi (10) Patent No.: US 10,458,475 B2
(45) Date of Patent: Oct. 29, 2019

(54) OIL MIST CONCENTRATION MANAGEMENT APPARATUS, OIL MIST MANAGEMENT SYSTEM, AND OIL MIST MANAGEMENT METHOD

(71) Applicant: FANUC CORPORATION, Yamanashi (JP)

(72) Inventor: Daisuke Nakanishi, Yamanashi (JP)

(73) Assignee: FANUC CORPORATION, Yamanashi (JP)

( * ) Notice: Subject to any disclaimer, the term of this patent is extended or adjusted under 35 U.S.C. 154(b) by 232 days.

(21) Appl. No.: 15/697,673

(22) Filed: Sep. 7, 2017

(65) Prior Publication Data

US 2018/0073563 A1 Mar. 15, 2018

(30) Foreign Application Priority Data

Sep. 9, 2016 (JP) .................................. 2016-176491

(51) Int. Cl.
| | |
|---|---|
| *F16C 33/66* | (2006.01) |
| *F16N 7/32* | (2006.01) |
| *G01N 11/06* | (2006.01) |
| *F16N 29/04* | (2006.01) |

(52) U.S. Cl.
CPC ...... *F16C 33/6674* (2013.01); *F16C 33/6662* (2013.01); *F16N 7/32* (2013.01); *F16N 29/04* (2013.01); *G01N 11/06* (2013.01); *Y02P 90/10* (2015.11); *Y02P 90/14* (2015.11)

(58) Field of Classification Search
CPC .... F16C 33/6674; F16C 33/6662; F16N 7/32; F16N 29/04; Y02P 90/10; Y02P 90/14; G01N 11/06
See application file for complete search history.

(56) References Cited

U.S. PATENT DOCUMENTS

| | | | | |
|---|---|---|---|---|
| 3,207,026 A | * | 9/1965 | Lovie | F01M 11/10 137/625.23 |
| 3,587,079 A | * | 6/1971 | Obergefell | G01N 21/534 340/506 |
| 4,213,044 A | | 7/1980 | Perrotta | |
| 6,161,649 A | * | 12/2000 | Cotler | B05B 7/0012 184/58 |
| 9,050,957 B2 | * | 6/2015 | Minato | B60T 13/662 |
| 10,221,732 B2 | * | 3/2019 | Kurata | F01M 1/08 |

(Continued)

FOREIGN PATENT DOCUMENTS

| | | |
|---|---|---|
| JP | 2002-239323 A | 8/2002 |
| JP | 2005-106017 A | 4/2005 |

(Continued)

*Primary Examiner* — Michael A Riegelman
(74) *Attorney, Agent, or Firm* — Hauptman Ham, LLP (57) ABSTRACT

An oil mist management system includes a machine tool, an oil mist concentration measuring apparatus for measuring concentration of oil mist, and a flow meter for detecting the flow rate of coolant, in each of a plurality of areas. A data processing apparatus determines whether distribution of the oil mist in the plurality of areas is normal or abnormal on an area-by-area basis, based on the concentration of the oil mist and the flow rate of coolant in each of the plurality of areas, and identifies an abnormal area. Further, the oil mist management system notifies a user of the abnormal area by an output device.

6 Claims, 5 Drawing Sheets

(56) References Cited

U.S. PATENT DOCUMENTS

| | | | |
|---|---|---|---|
| 2005/0264793 A1* | 12/2005 | Roders | B23Q 17/2485 356/36 |
| 2007/0071381 A1* | 3/2007 | Neumeier | B23Q 11/123 384/373 |
| 2012/0199097 A1* | 8/2012 | Sugiyama | F01M 1/04 123/196 CP |
| 2012/0291535 A1* | 11/2012 | Maloney | G01N 33/30 73/114.57 |
| 2013/0125624 A1* | 5/2013 | Gnauert | F01M 11/10 73/31.01 |
| 2013/0139782 A1* | 6/2013 | Takahashi | F01M 1/04 123/196 R |
| 2014/0271118 A1* | 9/2014 | Junod | F02C 7/06 415/1 |
| 2015/0000388 A1* | 1/2015 | Gnauert | G01M 15/042 73/114.56 |
| 2016/0089758 A1* | 3/2016 | Fujimoto | G05B 19/414 700/180 |
| 2017/0022881 A1* | 1/2017 | Matsumoto | F01P 7/16 |
| 2018/0023762 A1* | 1/2018 | Kato | F01D 25/18 184/6.4 |
| 2018/0073563 A1* | 3/2018 | Nakanishi | F16C 33/6662 |
| 2018/0074480 A1* | 3/2018 | Nakanishi | G05B 19/41875 |
| 2019/0086382 A1* | 3/2019 | Inaba | F16C 33/6625 |

FOREIGN PATENT DOCUMENTS

| | | |
|---|---|---|
| JP | 2012-43952 A | 3/2012 |
| JP | 2016-64482 A | 4/2016 |

\* cited by examiner

| AREA | OIL MIST CONCENTRATION (mg/m$^3$) | RANK |
|---|---|---|
| A | 3.0 | 1 |
| B | 2.5 | 2 |
| C | 2.0 | 3 |
| D | 1.5 | 4 |
| E | 1.0 | 5 |
| F | 0.5 | 6 |

FIG. 3B

| AREA | COOLANT AVERAGE FLOW RATE (L/min) | RANK |
|---|---|---|
| A | 10 | 3 |
| B | 30 | 1 |
| C | 5 | 4 |
| D | 20 | 2 |
| E | 3 | 5 |
| F | 1 | 6 |

FIG. 3C

| AREA | RANK (OIL MIST CONCENTRATION) | AREA | RANK (COOLANT AVERAGE FLOW RATE) | AREA HAVING LOW VENTILATION PERFORMANCE |
|---|---|---|---|---|
| A | 1 | A | 3 | * |
| B | 2 | B | 1 | |
| C | 3 | C | 4 | * |
| D | 4 | D | 2 | |
| E | 5 | E | 5 | |
| F | 6 | F | 6 | |

FIG. 4

OIL MIST CONCENTRATION MANAGEMENT APPARATUS, OIL MIST MANAGEMENT SYSTEM, AND OIL MIST MANAGEMENT METHOD

CROSS-REFERENCE TO RELATED APPLICATION

This application is based upon and claims the benefit of priority from Japanese Patent Application No. 2016-176491 filed on Sep. 9, 2016, the contents of which are incorporated herein by reference.

BACKGROUND OF THE INVENTION

Field of the Invention

The present invention relates to an oil mist concentration management apparatus, an oil mist management system, and an oil mist management method for managing a state of oil mist generated in a factory.

Description of the Related Art

Machine tools (metal machining devices) for metal machining are used to blow cutting fluid onto workpieces in machining (cutting), etc. to thereby improve the lubricating performance of the tools, prevent generation of dust, and cool the tools and/or the workpieces, for example. Therefore, oil mist (cutting fluid in the form of mist) is dispersed in the air around the machine tool. Since this oil mist may cause operation failures, e.g., in the drive control of the apparatus, it is desired to eliminate the oil mist as much as possible.

For example, in a machine tool disclosed in Japanese Laid-Open Patent Publication No. 2016-064482, concentration of the oil mist is measured in a control panel of the machine tool, and concentration of the oil mist is adjusted based on the measurement result.

SUMMARY OF THE INVENTION

In the metal machining factory, normally, a plurality of machine tools are provided, and various types of machining are performed by the machine tools. The quantity of cutting fluid used by the machining tool may vary depending on the type of machining performed by the machining tool. Therefore, by the floating oil mist dispersed from the machine tools, oil mist concentration is high in some areas, and oil mist concentration is low in some other areas in the factory. In order to achieve improvement in the working environment in the factory, it is important to recognize areas in the factory where the ventilation performance is low, and the concentration of the oil mist tends to become high.

The present invention has been made taking the above circumstances into account, and an object of the present invention is to provide an oil mist concentration management apparatus, an oil mist management system, and an oil mist management method which make it possible to achieve improvement in the working environment in a factory by suitably identifying the state of the oil mist distribution in a plurality of areas, on the area by area basis.

In order to achieve the above object, an oil mist concentration management apparatus according to the present invention includes a state quantity acquisition unit configured to acquire a state quantity regarding a running state of a machine provided in each of a plurality of areas, a concentration acquisition unit configured to acquire a concentration of oil mist measured in each of the plurality of areas, an identifying unit configured to identify whether distribution of the oil mist in the plurality of areas is normal or abnormal on an area-by-area basis, based on the state quantity of the machine in each of the plurality of areas and the concentration of the oil mist in each of the plurality of areas, and a notification processing unit configured to notify a user of an abnormal area which has been identified as abnormal by the identifying unit.

In the above structure, the oil mist concentration management apparatus can suitably specify the state of the distribution of the oil mist in the plurality of areas on the area by area basis, based on the state quantity of the machine obtained by the state quantity acquisition unit and the concentration of the oil mist obtained by the concentration acquisition unit. That is, normally, if the state quantity regarding the running state of the machine is large, since a large quantity of oil mist is dispersed, concentration of the oil mist becomes high. However, in a case where the state quantity is small and the concentration of the oil mist is high in an area, it is possible to presume that the concentration of the oil mist has been increased due to the low ventilation performance in the area. Therefore, the oil mist concentration management apparatus can suitably recognize the abnormal area together with factors for the high oil mist concentration, and the notification processing unit can notify the user of this abnormal area. In this manner, the user can achieve improvement in the working environment in the factory. For example, improvement in the running efficiency of the factory is expected.

In this case, as the state quantity regarding the running state of the machine, the identifying unit may use the flow rate of coolant used at the time of operating the machine.

The oil mist concentration management apparatus uses the flow rate of the coolant as the state quantity regarding the running state of the machine. Since the flow rate of the coolant is highly correlated with the quantity of the generated oil mist, it is possible to identify the abnormal area even more accurately.

In addition to the above structure, preferably, the oil mist concentration management apparatus further includes an integrated quantity calculation unit configured to calculate integrated quantity of the coolant during operation of the machine based on the flow rate of the coolant detected by a flow meter, and an average flow rate calculation unit configured to calculate the average flow rate of the coolant used by the machine based on the integrated quantity and a time period for which the machine is operated, and the identifying unit uses the average flow rate of the coolant as the state quantity of the machine in each of the plurality of areas.

If the machining speed of the machine is high, since a large quantity of coolant is used, the average flow rate of the coolant becomes high. Conversely, if the machining speed of the machine is low, since a small quantity of coolant is used, the average flow rate of the coolant becomes low. That is, since the oil mist concentration management apparatus uses the average flow rate which is more highly correlated with the oil mist concentration, it is possible to identify the abnormal area more accurately.

In this regard, the identifying unit may include a concentration rank determination unit configured to determine a relative concentration rank regarding the concentration of the oil mist among the plurality of areas, based on the concentration of the oil mist in each of the plurality of areas.

Further, the oil mist concentration management apparatus determines the relative concentration ranking among the plurality of areas by the concentration rank determination unit. Thus, it is possible to recognize the relative difference in oil mist concentration on the area by area basis. Therefore, it is possible to easily identify an abnormal area.

Further, the identifying unit may further include a state quantity rank determination unit configured to determine a relative state quantity rank regarding the state quantity among the plurality of areas, based on the state quantity of the machine in each of the plurality of areas.

Further, the oil mist concentration management apparatus determines the relative flow rate ranking among the plurality of areas by the state quantity rank determination unit. Therefore, it is possible to recognize the relative difference in the state quantity of the machine on the area by area basis. Thus, by using the concentration ranking and the state quantity ranking in combination, it is possible to identify the abnormal area even more easily.

Further, preferably, the identifying unit further includes a rank comparison unit configured to compare the concentration rank and the state quantity rank to thereby extract an area having a match or a mismatch between the concentration rank and the state quantity rank, and determine that the area having the mismatch is the abnormal area.

If there is any mismatch between the concentration rank and the state quantity rank, the ventilation performance of an area having the mismatch is different from the ventilation performance of the other areas where the concentration rank matches the flow rate rank. Therefore, the oil mist concentration management apparatus can easily recognize the difference in the ventilation performance on the area by area basis.

Furthermore, if there is an area where the state quantity rank is lower than the concentration rank, the rank comparison unit may identify that ventilation performance of the area is low.

If the state quantity rank is lower than the concentration rank in an area, though the state quantity regarding the running state of the machine is low, the concentration of the oil mist is high in the area. Therefore, the rank comparison unit can easily and reliably recognize that the ventilation performance is low.

Preferably, the oil mist concentration management apparatus further includes a determination unit configured to determine whether the concentration of the oil mist acquired by the concentration acquisition unit is larger than a threshold value that is retained beforehand, and if the determination unit determines that there is an area where the concentration of the oil mist is larger than the threshold value, the identifying unit identifies that the area is the abnormal area.

The determination unit can determine that the concentration of the oil mist is increased to some extent, and thus, the user can recognize the relative difference in the ventilation performance on the area by area basis even more accurately.

Further, in order to achieve the above object, an oil mist management system according to the present invention includes a machine provided in each of a plurality of areas, a detection device provided in each of the plurality of areas, and configured to detect a state quantity regarding a running state of the machine, a concentration measuring apparatus provided in each of the plurality of areas, and configured to measure concentration of oil mist in each of the plurality of areas, an oil mist concentration management apparatus configured to identify whether distribution of the oil mist in the plurality of areas is normal or abnormal on an area-by-area basis, based on the state quantity of the machine in each of the plurality of areas and the concentration of the oil mist in each of the plurality of areas, and an output device configured to notify a user of an abnormal area which has been identified as abnormal by the oil mist concentration management apparatus.

Further, in order to achieve the above object, an oil mist management method of managing oil mist in a factory having a machine in each of a plurality of areas, by an oil mist concentration management apparatus is provided. The method includes a state quantity acquisition step of acquiring a state quantity regarding a running state of the machine provided in each of the plurality of areas, a measurement data acquisition step of acquiring concentration of oil mist measured in each of the plurality of areas, a data processing step of identifying whether distribution of the oil mist in the plurality of areas is normal or abnormal on an area-by-area basis, based on the state quantity of the machine in each of the plurality of areas and the concentration of the oil mist in each of the plurality of areas, and a notification step of notifying a user of an abnormal area which has been identified as abnormal in the data processing step.

In the oil mist concentration management apparatus, the oil mist management system, and the oil mist management method according to the present embodiment, by suitably determining the state of the distribution of the oil mist in the plurality of areas on the area-by-area basis, it is possible to facilitate improvement in the working environment in the factory.

The above and other objects, features and advantages of the present invention will become more apparent from the following description when taken in conjunction with the accompanying drawings in which a preferred embodiment of the present invention is shown by way of illustrative example.

DESCRIPTION OF THE PREFERRED EMBODIMENTS

Hereinafter, a preferred embodiment of an oil mist concentration management apparatus, an oil mist management system, and an oil mist management method will be described in detail with reference to the accompanying drawings.

Figure 1:
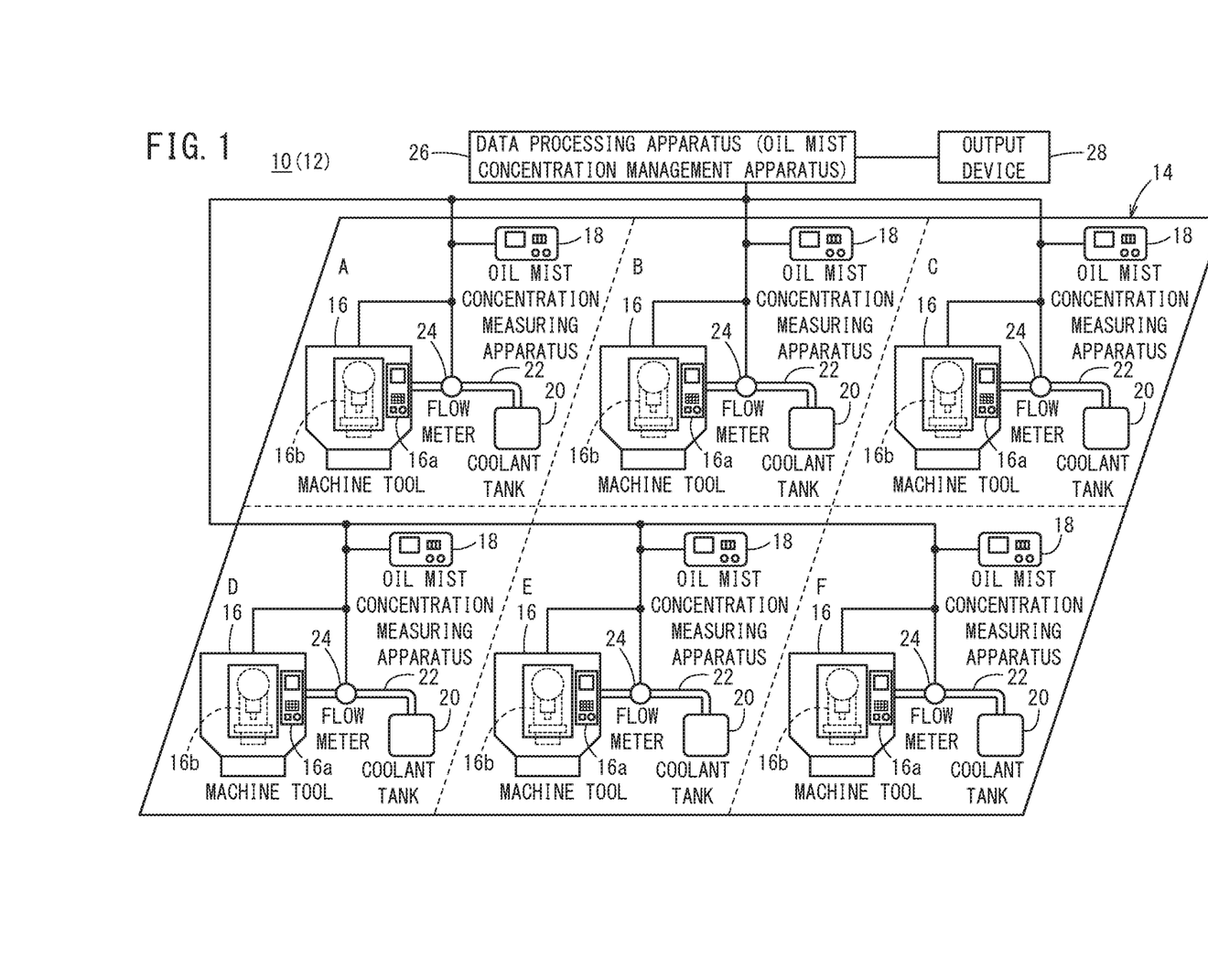
FIG. 1 is a view schematically showing overall structure of an oil mist management system according to one embodiment of the present invention.

As shown in FIG. 1, an oil mist management system 10 according to one embodiment of the present invention is provided in a metal machining factory 12 (hereinafter also simply referred to as the factory 12). The oil mist management system 10 is provided as a system for monitoring the state of oil mist floating in a machining room 14 of the factory 12. In particular, the oil mist management system 10 recognizes the distribution state of the oil mist in the machining room 14 on an area-by-area basis, and recognizes the difference in ventilating performance between the areas to facilitate improvement of the working environment.

In the machining room 14 of the factory 12, for example, a plurality of machine tools (machines) 16 (metal machining devices) are provided. Each of the machine tools 16 cuts metal material into workpieces having predetermined shapes, under control of a control device 16a. As described above, at the time of machining (cutting), the cutting fluid, etc. used by the machine tools 16 is dispersed or scattered into oil mist, and the oil mist floats in the machining room 14. The oil mist management system 10 divides the machining room 14 into a plurality of (six, in FIG. 1) areas, and monitors the floating oil mist. Hereinafter, for ease of explanation, alphabets A to F are assigned to the six areas, respectively. These areas will be referred to as the area A, the area B, the area C, . . . , respectively.

As a method of dividing the machining room 14 into the plurality of areas A to F, for example, the machining room 14 is divided into areas for each of the machine tools 16. Alternatively, in a case where the machining room 14 is partitioned by walls, resin panels, or the like into spaces, each of the partitioned spaces may be regarded as one area. Alternatively, even if the machining room 14 is not partitioned spatially, the machining room 14 may be virtually divided into the areas A to F which are rectangular (or square) areas having a predetermined size.

Each of the areas A to F is provided with one or more machine tool 16 and an oil mist concentration measuring apparatus 18. In this case, different types of machine tools 16 may be provided in the areas A to F. Alternatively, the same type of machine tools 16 may be provided in the areas A to F. In the following description, the same type of machine tools 16 are provided in the areas A to F. However, the types of the machine tools 16 are not limited as long as there is one or more machine tool which performs machining operation under the environment where the oil mist is dispersed.

Each of the areas A to F is provided with a coolant tank 20 for storing coolant (cooling medium) used as cutting oil during machining operation of the machine tools 16. The machine tool 16 and the coolant tank 20 are connected by a pipe 22. A flow meter 24 for detecting the flow rate (supply rate) of the coolant is provided at an intermediate position of the pipe 22. In a case where a plurality of machine tools 16 are provided in one area, the coolant for the plurality of machine tools 16 should be stored altogether in one coolant tank 20, and the flow meter 24 should be configured to detect the total flow rate of the coolant for the plurality of machine tools 16. Alternatively, the coolant tank 20 and the flow meter 24 may be provided for each of the plurality of machine tools 16, and detection values of the respective flow meters 24 may be managed altogether by a computer (not shown).

Further, in the factory 12 (e.g., management room), a data processing apparatus 26 (oil mist concentration management apparatus) is provided. The data processing apparatus 26 performs information communication through communication means such as a LAN among the machine tool 16, the oil mist concentration measuring apparatus 18 and the flow meter 24 in each of the areas A to F. Further, the data processing apparatus 26 is connected to an output device 28. The output device 28 provides information for a user who manages the factory 12. Examples of the output device 28 include a monitor and/or a speaker, and a notification light provided in each of the areas.

The machine tool 16 provided in each of the areas A to F is used for machining metal material, and includes the control device 16a described above, and a drive unit 16b for driving a tool by a servo motor or a linear motor. The control device 16a controls operation of a tool (drive unit 16b) based on an internally stored machining program, and forms a workpiece into a predetermined shape.

One end of the pipe 22 is connected to the machine tool 16, and the other end of the pipe 22 is connected to the coolant tank 20. At the time of machining operation, the coolant from the coolant tank 20 is supplied to the machine tool 16 through the pipe 22. The machine tool 16 performs machining operation of a workpiece while blowing the coolant as the cutting fluid onto the workpiece. It should be noted that the coolant tank 20, the pipe 22, and the flow meter 24 may be provided inside the machine tool 16.

A storage bath is used as the coolant tank 20. The storage bath has a volume sufficient to store the coolant. Further, the coolant tank 20 has a pump (not shown) driven by the control device 16a of the machine tool 16. Using the pump, a proper quantity of coolant is supplied to the machine tool 16.

The flow meter 24 detects the quantity of fluid flowing from the coolant tank 20 to the machine tool 16. This flow meter 24 is a detection device configured to detect the flow rate (supply rate) of the coolant as a state quantity related to the running state of the machine tool 16. The type of the flow meter 24 is not limited specifically as long as the flow meter 24 can measure the flow rate of the coolant. An electromagnetic flow meter, a differential pressure type flow meter, an ultrasonic flow meter, a coriolis flow meter, etc. may be used as the flow meter 24.

Further, a flow rate integrating unit 30 (integrated quantity calculation unit: see FIG. 2) for integrating quantity of flow of the detected coolant is provided inside the flow meter 24. The flow rate integrating unit 30 is operated when the machine tool 16 is driven. From the beginning of the machining operation, the flow rate (quantity) of the coolant used by the machine tool 16 during the operation is integrated to calculate the integrated quantity of the coolant during the operation. Then, based on a command from the data processing apparatus 26, the flow meter 24 transmits the integrated quantity data Di calculated by the flow rate integrating unit 30 to the data processing apparatus 26. It should be noted that the flow rate integrating unit 30 may be provided on the data processing apparatus 26 and the control device 16a of the machine tool 16.

Further, the oil mist concentration measuring apparatus 18 in each of the areas A to F measures the concentration of the oil mist dispersed and floating around this oil mist concentration measuring apparatus 18, and transmits the measurement data Dm (oil mist concentration) to the data processing apparatus 26. Basically, the oil mist concentration measuring apparatus 18 may be provided at any position in the area for installation of the machine tool 16. However, more preferably, the oil mist concentration measuring apparatus 18 should be provided at a position adjacent to the machine tool 16 in the same area, or at a position where the ventilation performance is expected to be low.

According to a possible principle of the oil mist concentration measuring apparatus 18 of this type, for example, air containing the oil mist is introduced thereinto, and the introduced oil mist is electrified, so that the mist is attracted to a piezoelectric element. Based on the resulting frequency change of the piezoelectric element at this time, the concentration is processed into a numeric value. Alternatively, according to another possible principle of the oil mist concentration measuring apparatus 18, a filter (not shown) may be provided, and the weight change of the filter is measured to process the concentration of the oil mist into a numeric value. In still another example, air containing the oil mist is introduced thereinto, and the introduced oil mist is irradiated with a laser in the optical system, so that the laser is scattered. Based on the scattered light, the concentration is processed into a numeric value.

The data processing apparatus 26 recognizes the relative state of the oil mist in each of the plurality of areas A to F based on the oil mist concentration in each of the plurality of areas A to F and a state quantity regarding the running state of the machine tool 16 in each of the plurality of areas A to F. In the embodiment of the present invention, the state quantity regarding the running state of the machine tool 16 is the flow rate of the coolant.

For example, a computer made up of a processor, an input/output interface (not shown), and a memory 32 (see FIG. 2) is used as the data processing apparatus 26. Alternatively, a management computer and/or a server which manages the entire factory 12, or a control computer, etc. which monitors the state of the plurality of machine tools 16 in the machining room 14 may be used as the data processing apparatus 26. Further, an input device (not shown) is connected to the data processing apparatus 26. The user operates the input device as necessary, and can provide details of processes by the data processing apparatus 26 and retained data through the output device 28.

Figure 2:
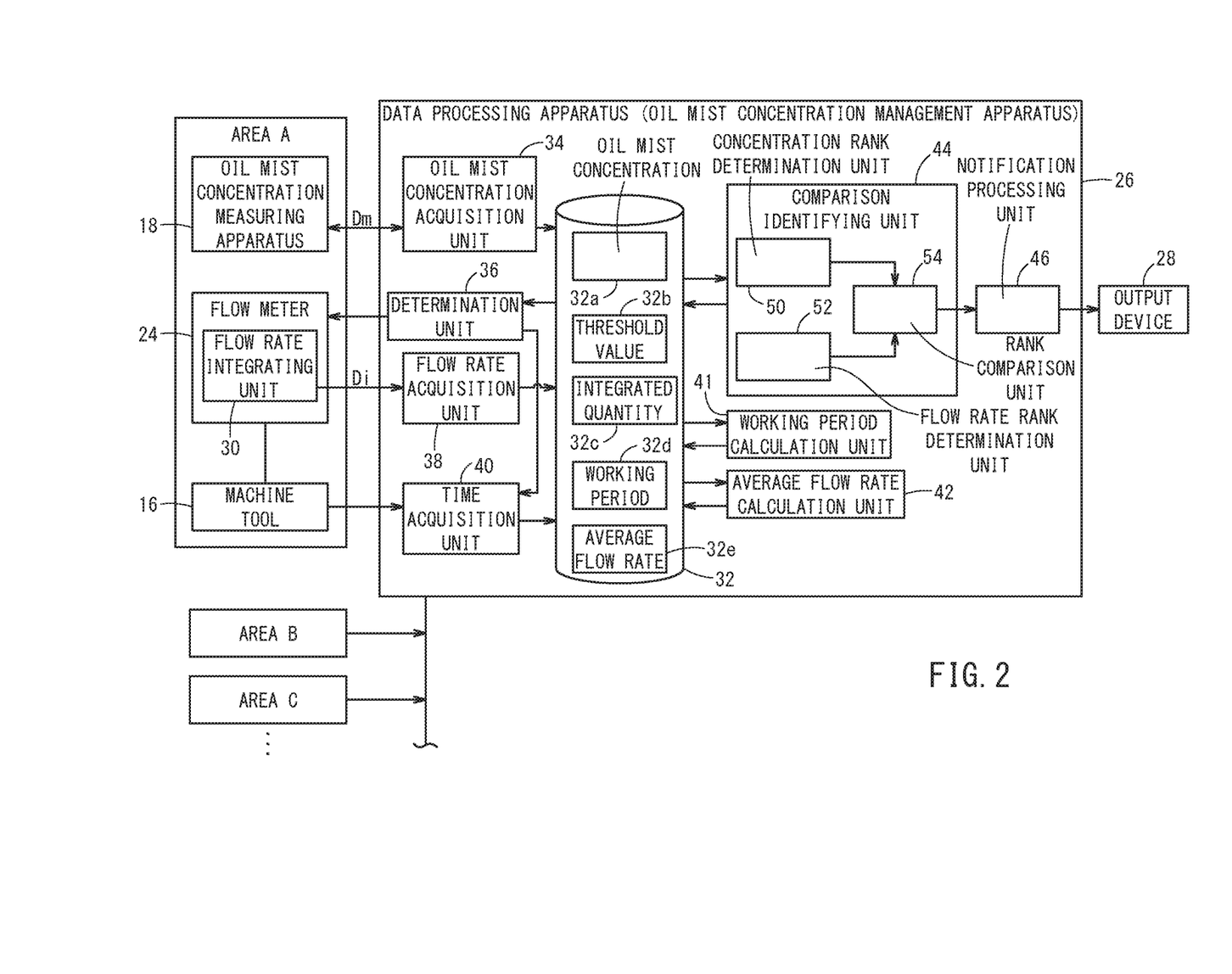
FIG. 2 is a functional block diagram when the oil mist management system in FIG. 1 is operated.

Further, the data processing apparatus 26 realizes a software functional unit which monitors the state of the oil mist in the factory 12, by the processor executing a control program (not shown) stored in the memory 32. More specifically, as shown in FIG. 2, the data processing apparatus 26 realizes an oil mist concentration acquisition unit 34, a determination unit 36, a flow rate acquisition unit 38 (state quantity acquisition unit), a time acquisition unit 40, a working period calculation unit 41, an average flow rate calculation unit 42, a comparison identifying unit 44 (identifying unit), and a notification processing unit 46.

The oil mist concentration acquisition unit 34 receives measurement data Dm of the oil mist from the oil mist concentration measuring apparatus 18 in each of the areas A to F. A database is created in a manner to associate the areas A to F with the oil mist concentrations, and stored in an oil mist concentration storage area 32*a* of the memory 32. For example, the oil mist concentration acquisition unit 34 acquires the measurement data Dm by providing a command to the oil mist concentration measuring apparatus 18 at a predetermined time period. At this time, in order to improve the efficiency of processing, the time period may be changed, e.g., by acquiring the oil mist concentration in a short sampling time period when the oil mist concentration is high, and acquiring the oil mist concentration in a long sampling time period when the oil mist concentration is low. Further, the oil mist concentration acquisition unit 34 may automatically obtain measurement data Dm from the oil mist concentration measuring apparatus 18.

The determination unit 36 determines the oil mist concentration of each of the areas A to F stored in the memory 32. More specifically, based on acquisition of the measurement data Dm, the determination unit 36 reads a threshold value Th for determining the oil mist concentration stored in a threshold value storage area 32*b* of the memory 32, and the oil mist concentration stored in the oil mist concentration storage area 32*a*, and then compares the threshold value Th with the oil mist concentration. The threshold value Th is determined beforehand as an averaged numeric value of the upper limit of the allowable oil mist concentration in the entire machining room 14. For example, 2.0 [mg/m$^3$] is determined as the threshold value Th. Further, the threshold value Th may be determined for each of the areas depending on the environment of each of the areas A to F.

If the determination unit 36 determines that the oil mist concentration in a certain area has become larger than the threshold value Th, the determination unit 36 operates the data processing apparatus 26 to implement recognition control for recognize the state of the oil mist in each of the areas A to F. When the oil mist concentration is the threshold value Th or less, recognition control is not implemented. This is because, when the oil mist concentration is low, the oil mist does not significantly affect the machine tool 16, and it is difficult to accurately recognize the difference of the ventilation performance on the area-by-area basis. At the time of implementing the recognition control, the determination unit 36 instructs the flow meter 24 of each of the areas A to F to transmit the integrated quantity data Di of the coolant, to the data processing apparatus 26.

The flow rate acquisition unit 38 stores the integrated quantity data Di of the coolant outputted from the flow meter 24 based on the instruction of the above described determination unit 36, and stores the integrated quantity data Di in an integrated quantity storage area 32*c* of the memory 32. It should be noted that the flow rate acquisition unit 38 may periodically acquire and update the integrated quantity data Di of the flow meter 24 regardless of processing by the determination unit 36.

When the machine tools 16 in the areas A to F start machining operations, the time acquisition unit 40 receives the start time from each of the machine tools 16, and stores the start time in a time storage area 32*d* of the memory 32. Further, the time acquisition unit 40 receives the determination time when implementation of recognition control is determined by the determination unit 36, and stores the determination time in the time storage area 32*d* of the memory 32.

The working period calculation unit 41 reads the determination time and the start time stored in the memory 32, and subtracts the start time from the determination time to thereby calculate the working period for each of the machine tools 16 of the areas A to F, and stores the working period in the time storage area 32*d* of the memory 32. In the embodiment of the present invention, the working period is calculated in minutes.

For each of the areas A to F, the average flow rate calculation unit 42 calculates the average flow rate per unit time (per minute) of the coolant used by the machine tools 16 of the areas A to F, based on determination about implementation of the recognition control by the determination unit 36. Specifically, the integrated quantity of the coolant stored in the memory 32 is divided by the working period calculated by the time acquisition unit 40 to thereby obtain the average flow rate of the coolant. The average flow rate of the coolant is calculated for each of the plurality of areas A to F. In a case where a plurality of machine tools 16 are provided in one area, the average flow rate of coolant used in the area is calculated. The average flow rate calculation unit 42 associates the calculated average flow rate in each of the areas A to F with each of the areas A to F to create a database, and stores the database in an average flow rate storage area 32*e* of the memory 32.

The comparison identifying unit 44 is a functional unit configured to read the oil mist concentration and the coolant average flow rate of each of the areas A to F stored in the memory 32, and identify the difference in the relative ventilation performance among the areas A to F. Hereinafter, the principle of this identification procedure will be described.

Normally, as the running quantity (state quantity regarding the running state of the machine tool 16) becomes larger, so the quantity of cutting fluid used by the machine tool 16 becomes larger. Therefore, the quantity of oil mist dispersed around the machine tool 16 is increased as well. Conversely, if the running quantity is small, since the quantity of the cutting fluid used by the machine tool 16 becomes small, the quantity of oil mist dispersed around the machine tool 16 is decreased as well. However, the ventilation performance in the machining room 14 is affected by an air conditioning system, the layout (positions) of the machine tools 16 and an oil mist removing apparatus, partitions, etc. Therefore, the oil mist concentration tends to become high in some positions in the machining room 14 as described above. Further, the ventilation performance in the machining room 14 may change simply by temporarily placing baggage, etc. therein. Therefore, it is desired to continue monitoring as much as possible while the factory 12 is running.

In this regard, assuming that there is an area where a large quantity of oil mist is dispersed (i.e., the concentration of the oil mist is high) even if the running quantity of the machine tool 16 is small, the ventilation performance of the area can be regarded as being low. Conversely, assuming that there is an area where a small quantity of oil mist is dispersed even if the running quantity of the machine tool 16 is large, the ventilation performance of the area can be regarded as being high. Thus, based on the oil mist concentration and the running quantity of the machine tool 16, the oil mist management system 10 identifies an area having low ventilation performance.

In the embodiment of the present invention, the running quantity of the machine tool 16 is obtained by the average flow rate of the coolant which is highly correlated with the oil mist concentration. That is, if the running quantity is large, the machining rate of machining the workpiece is high, and a large quantity of the cutting fluid is used. Therefore, the average flow rate of the coolant becomes high. Conversely, if the running quantity is small, the machining rate of machining the workpiece is low, and a small quantity of the cutting fluid is used. Therefore, the average flow rate of the coolant becomes low.

In view of the above, the oil mist management system 10 checks whether or not the level of the oil mist concentration matches the level of the average coolant flow rate on the area by area basis. In this manner, the oil mist management system 10 can recognize the state of oil mist distribution. Therefore, at the time of implementing recognition control, a concentration rank determination unit 50, a flow rate rank determination unit 52 (state quantity rank determination unit), and a rank comparison unit 54 are provided inside the comparison identifying unit 44.

Figure 3A:
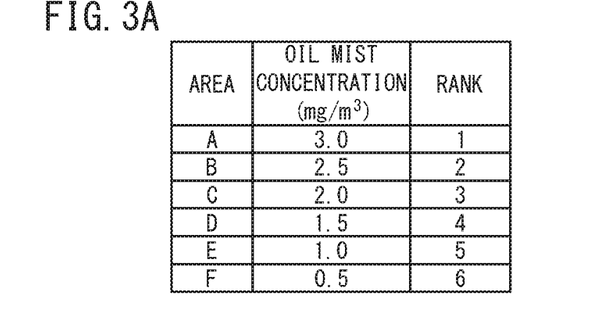
FIG. 3A is a table showing a manner of determining ranks of the oil mist concentration by a concentration rank determination unit.

The concentration rank determination unit 50 reads the database of the oil mist concentration of each of the areas A to F stored in the memory 32, and determines the ranking of the oil mist concentrations of the areas. For example, as shown in FIG. 3A, it is assumed that the concentration data of the area A is 3.0 [mg/m$^3$], the concentration data of the area B is 2.5 [mg/m$^3$], the concentration data of the area C is 2.0 [mg/m$^3$], the concentration data of the area D is 1.5 [mg/m$^3$], the concentration data of the area E is 1.0 [mg/m$^3$], and the concentration data of the area F is 0.5 [mg/m$^3$]. In this case, the concentration rank determination unit 50 gives ranks 1 to 6 in the order of A to F.

Figure 3B:
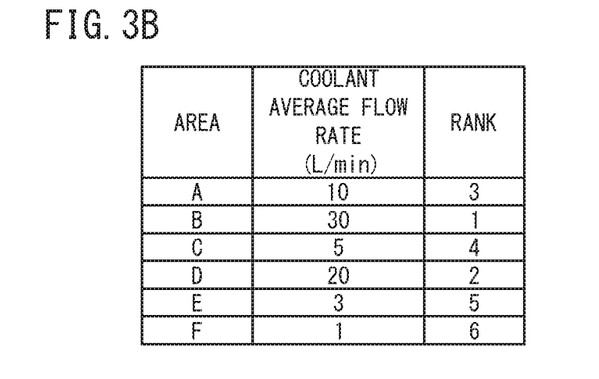
FIG. 3B is a table showing a manner of determining ranks of the average flow rate of coolant by a flow rate rank determination unit.

The flow rate rank determination unit 52 reads the database of the average flow rate of the coolant of the areas A to F stored in the memory 32, and determines the ranking of the average coolant flow rates of the areas. For example, as shown in FIG. 3B, it is assumed that the average flow rate data in the area A is 10 [L/min], the average flow rate data in the area B is 30 [L/min], the average flow rate data in the area C is 5 [L/min], the average flow rate data in the area D is 20 [L/min], the average flow rate data in the area E is 3 [L/min], and the average flow rate data in the area F is 1 [L/min]. In this case, the flow rate rank determination unit 52 determines that the area B having the highest average flow rate is the first rank, the area D having the second highest average flow rate is the second rank, the area A having the third highest average flow rate is the third rank, the area C having the fourth highest average flow rate is the fourth rank, the area E having the fifth highest average flow rate is the fifth rank, and the area F having the sixth highest average flow rate is the sixth rank.

Figure 3C:
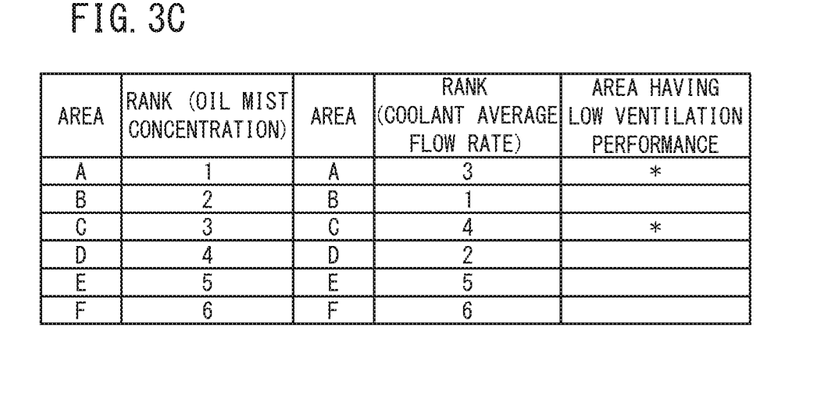
FIG. 3C is a table showing comparison between the concentration rank and the flow rate rank by a rank comparison unit.

As shown in FIG. 3C, the rank comparison unit 54 compares the ranks of the oil mist concentration of the areas A to F determined by the concentration rank determination unit 50 with the ranks of the coolant average flow rate of the areas A to F determined by the flow rate rank determination unit 52 to thereby identify the area(s) having low ventilation performance. Hereinafter, the rank of the oil mist concentration in each of the areas A to F will be referred to as the concentration rank, and the rank of the coolant average flow rate in each of the areas A to F will be referred to as the flow rate rank (state quantity rank).

Specifically, the rank comparison unit 54 identifies an area where the flow rate rank is lower than the concentration rank (i.e., an area in which the concentration rank< the flow rate rank in the numeric values of the ranks). In the illustrated example, as indicated by asterisks (*), the areas A and C are identified. That is, the area where the flow rate rank is lower than the concentration rank is an area where a large quantity of oil mist is present even though the running quantity of the machine tool 16 is small. Thus, it is possible to presume that the area is an abnormal area having low ventilation performance. Further, it is presumed that an area where the flow rate rank is equal to the concentration rank (concentration rank=flow rate rank) is an area having the normal relationship between the running quantity of the machine tool 16 and the oil mist concentration. When identifying the area(s) having the low ventilation performance by the above comparison, the rank comparison unit 54 transmits the identification result to the notification processing unit 46.

It should be noted that the rank comparison unit 54 may identify an area where the concentration rank is higher than the flow rate rank (concentration rank> flow rate rank) at the time of comparison, and recognize the area having high ventilation performance as an abnormal area. In this manner, the oil mist management system 10 may notify the user of the area having the high ventilation performance, and prompt the user to take a suitable action (e.g., improvement of the air conditioning system) to thereby achieve a uniform distribution of the oil mist concentration in the entire machining room 14.

When the notification processing unit 46 receives information that an area having low ventilation performance has been identified, from the comparison identifying unit 44, the notification processing unit 46 issues a notification to the effect that the area has low ventilation performance, through the output device 28. For example, the notification processing unit 46 generates abnormality occurrence image information to be displayed on a monitor of the output device 28. This abnormality occurrence image information includes a map and a plurality of areas in the machining room 14. For example, by displaying the area(s) having low ventilation performance among the plurality of areas in warning colors or in a blinking manner, a warning is given to the user who checks the monitor, in order to draws the user's attention. Further, the output device 28 may output an alarm concerning the area having the low ventilation performance through a speaker or a notification light.

The oil mist management system 10 according to the embodiment of the present invention basically has the structure as described above. Hereinafter, the effects and advantages of the oil mist management system 10 will be described below.

At the time of running of the factory 12, operation of the machine tool 16, the oil mist concentration measuring apparatus 18 and the flow meter 24 is started by the user on the area by area basis. Therefore, the machine tool 16 is placed in a condition where machining can be started, and the oil mist concentration measuring apparatus 18 is placed in a state where the oil mist concentration around the apparatus can be measured. The flow meter 24 is placed in a condition where the flow volume of the coolant used by the machine tool 16 can be integrated. Further, the oil mist management system 10 operates the data processing apparatus 26 to implement the control for recognizing the state of the oil mist floating in the machining room 14.

Figure 4:
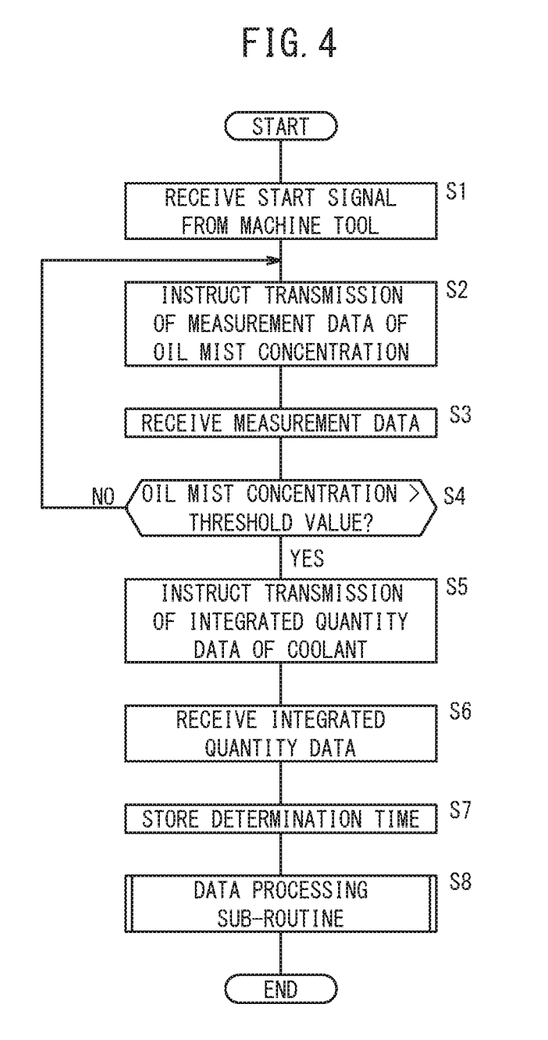
FIG. 4 is a flow chart showing a process flow of a data processing apparatus of FIG. 2.

As shown in FIG. 4, the data processing apparatus 26 receives information about the start signal and the start time, after starting operation, from the machine tool 16 of the area where machining operation has been started (step S1). As a result, the data processing apparatus 26 recognizes operation of the machine tool 16 in each of the areas A to F defined beforehand by dividing the machining room 14, and the time acquisition unit 40 stores the received start time in the memory 32.

Next, the oil mist concentration acquisition unit 34 outputs a transmission command of the measurement data Dm at each predetermined timing, to the oil mist concentration measuring apparatus 18 in each of the areas A to F (step S2). Based on this command, the oil mist concentration measuring apparatus 18 measures the oil mist concentration, and outputs the measurement data Dm. Thus, the oil mist concentration acquisition unit 34 receives the measurement data Dm (step S3: measurement data acquisition step), and stores the measurement data Dm in the memory 32 as oil mist concentration.

The determination unit 36 of the data processing apparatus 26 compares the received oil mist concentration with a threshold value Th, which is retained beforehand, and determines whether or not the oil mist concentration is larger than the threshold value Th (step S4). Then, in a case where the oil mist concentration is the threshold value Th or less, the routine returns to step S2. If the oil mist concentration is larger than the threshold value Th, the control proceeds to step S5, in which recognition control to recognize the state of the oil mist of each of the areas A to F is performed.

In step S5, the determination unit 36 outputs a transmission command of the integrated quantity data Di of the coolant to the flow meter 24 of each of the areas A to F. The flow meter 24 of each of the areas A to F detects the flow rate of the coolant during operation of the machine tool 16, and the flow rate integrating unit 30 calculates integration data of the coolant. Therefore, the flow rate acquisition unit 38 of the data processing apparatus 26 receives the integrated quantity data Di of the coolant from the flow meter 24 of each of the areas A to F (step S6: state quantity acquisition step).

Further, the time acquisition unit 40 receives the determination time from the determination unit 36, and stores the determination time in the memory 32 (step S7). Thereafter, the data processing apparatus 26 implements a data processing sub-routine for recognizing the state of the oil mist in each of the areas A to F (step S8: data processing step).

Figure 5:
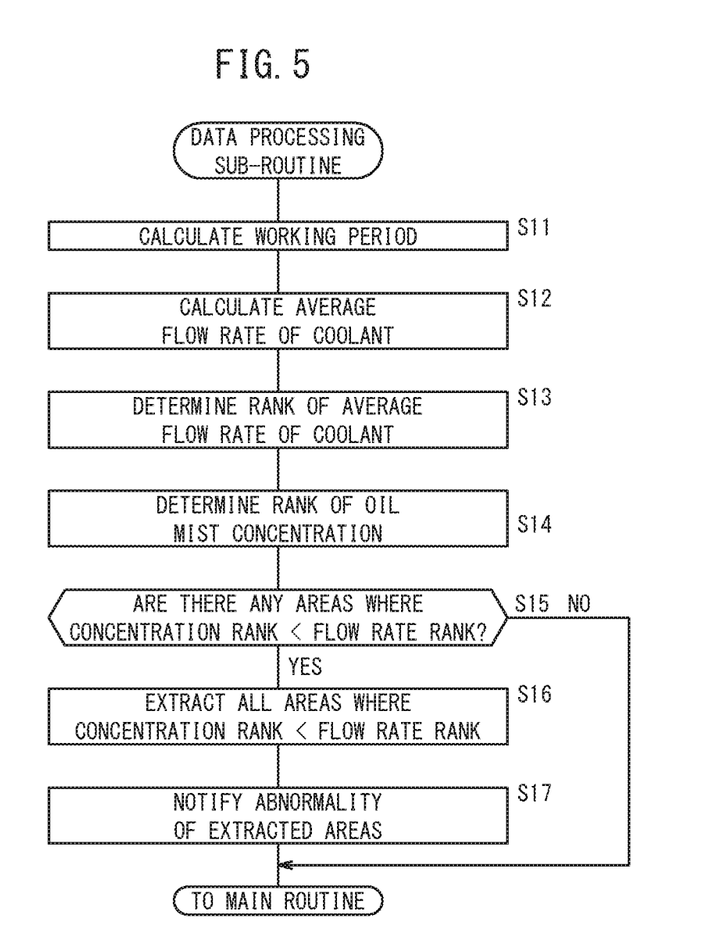
FIG. 5 is a flow chart showing a data processing subroutine of FIG. 4.

As shown in FIG. 5, in the data processing sub-routine, firstly, the working period calculation unit 41 calculates the working period of the machine tool 16 of each of the areas A to F based on the start time and the determination time of the machine tool 16 (step S11). Next, the average flow rate calculation unit 42 calculates the average flow rate of the coolant of each of the areas A to F based on the integrated quantity data Di of the coolant acquired in step S6 and the working period calculated by the time acquisition unit 40 in step S7 (step S12).

Then, the flow rate rank determination unit 52 of the comparison identifying unit 44 determines ranks of the average flow rate of the coolant of the areas A to F based on the calculated average flow rate of the coolant (step S13: see also FIG. 3B).

Further, the concentration rank determination unit 50 of the comparison identifying unit 44 determines ranks of the oil mist concentration of each of the areas A to F based on the oil mist concentration stored in the memory 32 (step S14: also see FIG. 3A). It should be noted that steps S11 to S13 may be performed concurrently with step S14.

Thereafter, the rank comparison unit 54 of the comparison identifying unit 44 compares the concentration rank and the flow rate rank of each of the areas A to F, and determines whether or not there is any area where the concentration rank is smaller than the flow rate rank (step S15). Then, if there is any area where the concentration rank is smaller than the flow rate rank, the routine proceeds to step S16. If there is no area where the concentration rank is smaller than the flow rate rank, the oil mist concentration matches the running quantity (coolant average flow rate) of the machine tool 16 in each of the areas A to F. Therefore, it is recognized that there is no problem in the ventilation performance in each of the areas A to F, and the data processing sub-routine is finished.

In step S16, the rank comparison unit 54 extracts all the areas where the concentration rank is smaller than the flow rate rank (see also FIG. 3C). Thereafter, the notification processing unit 46 generates notification contents (abnormality occurrence image information) regarding the extracted area, and notifies the information by issuing an alarm by the output device 28 (displays the abnormality occurrence image information on the monitor) (step S17: notification step). In this manner, the user can recognize the area having the low ventilation performance. By taking an action to decrease the oil mist concentration, it becomes possible to achieve improvement in the working environment.

When the data processing sub-routine is finished, the routine returns to the main routine shown in FIG. 4, and the process flow of the data processing apparatus 26 is finished. Further, in a case where the machine tools 16 in the areas A to F continue machining operation, the data processing apparatus 26 should repeat the above process flow again.

As described above, in the oil mist management system 10 and the oil mist management method, based on the state quantity (coolant average flow rate) regarding the oil mist concentration and the running state of the machine (e.g., the machine tool), it is possible to suitably specify the state of the oil mist concentration in the plurality of areas, on the area by area basis. That is, in the case where the coolant average flow rate is small and the oil mist concentration is high, the data processing apparatus 26 can presume that the oil mist concentration is high due to the low ventilation performance of the area. Therefore, since the user is notified of the abnormal area by the output device 28, the user can recognize the abnormal area, and it is possible to achieve improvement in the working environment in the machining room 14. For example, improvement in the running efficiency of the factory 12 is expected.

In this case, since the state quantity regarding the running state of the machine is the flow rate of the coolant, the oil mist management system 10 can detect the state quantity easily by the flow meter 24. Further, in the case where the machine is the machine tool 16, since the flow rate of the coolant is highly correlated with the quantity of the generated oil mist, it is possible to identify the abnormal area even more accurately. Further, since the data processing apparatus 26 uses the average flow rate which is more highly correlated with the oil mist concentration, it is possible to identify the abnormal area more accurately.

The data processing apparatus 26 determines the relative concentration ranks among the plurality of areas by the concentration rank determination unit 50. In this manner, the data processing apparatus 26 can recognize the relative difference of the oil mist concentration on the area by area basis. Further, since the data processing apparatus 26 determines the relative flow rate ranks among the plurality of areas by the flow rate rank determination unit 52, it is possible to recognize the relative difference in the average flow rate of the coolant used by the machine tool 16 on the area by area basis. Thus, by using the concentration rank and flow rate rank in combination, it is possible to identify the abnormal area even more easily. At this time, upon comparison between the concentration rank and the flow rate rank, if it is found that there is any mismatch between these ranks, the ventilation performance of the area having the mismatch is different from the ventilation performance of the other area where the concentration rank matches the flow rate rank. Therefore, the data processing apparatus 26 can easily recognize the difference in the ventilation performance on the area by area basis. Further, if the flow rate rank is lower than the concentration rank, even though the average flow rate of the coolant in the area is low, the oil mist concentration is high. Thus, it is possible to easily and reliably recognize that the ventilation performance is low in the area.

The oil mist management system and the oil mist management method according to the present invention are not limited to the above embodiments, and various applications and modifications can be adopted. For example, in the embodiment of the present invention, as the state quantity (running quantity) regarding the running state of the machine, though the flow rate of the coolant is utilized, the running quantity of the machine is not limited to the flow rate of the coolant. Alternatively, as the state quantity regarding the running state of the machine, electric power consumed while the machine tool is running may be used. Further, alternatively, as the state quantity regarding the running state of the machine, by referring to a machining program of the machine tool, the movement quantity of the tool or the processing load of the program may be extracted and used.

Further, for example, the data processing apparatus 26 may be configured not to determine the oil mist concentration by the determination unit 36. In this case, the data processing apparatus 26 may implement the above recognition control at the time after a certain period of time has elapsed from the start of running of the factory 12. Alternatively, the recognition control may be implemented periodically. Alternatively, the determination unit 36 may not only implement the recognition control at the time when the oil mist concentration in one area exceeds a threshold value, but also implement recognition control at the time when the oil mist concentration in a predetermined number of areas (e.g., three areas) exceeds the threshold value.

Further, in the case where the oil mist concentration in a certain area is extremely higher than the oil mist concentrations of the other areas, the data processing apparatus 26 may issue a warning (issues a notification of an alarming level which is higher than drawing the user's attention) by the output device 28.

The present invention is not limited to the above described embodiment. It is a matter of course that various modifications can be made without deviating from the scope of the present invention. For example, the oil mist management system 10 may not necessarily be applied to the factory 12. The oil mist management system 10 may be applicable to various environments where oil mist is generated.

What is claimed is:

1. An oil mist concentration management apparatus comprising:
 a state quantity acquisition unit configured to acquire a state quantity regarding a running state of a machine provided in each of a plurality of areas;
 a concentration acquisition unit configured to acquire a concentration of oil mist measured in each of the plurality of areas;
 an identifying unit configured to identify whether distribution of the oil mist in the plurality of areas is normal or abnormal on an area-by-area basis, based on the state quantity of the machine in each of the plurality of areas and the concentration of the oil mist in each of the plurality of areas; and
 a notification processing unit configured to notify a user of an abnormal area which has been identified as abnormal by the identifying unit,
 wherein
 the identifying unit uses, as the state quantity regarding the running state of the machine, a flow rate of coolant used at time of operating the machine,
 the identifying unit includes
 a concentration rank determination unit configured to determine a relative concentration rank regarding the concentration of the oil mist among the plurality of areas, based on the concentration of the oil mist in each of the plurality of areas,
 a state quantity rank determination unit configured to determine a relative state quantity rank regarding the state quantity among the plurality of areas, based on the state quantity of the machine in each of the plurality of areas,
 a rank comparison unit configured to compare the concentration rank and the state quantity rank to thereby extract an area having a match or a mismatch between the concentration rank and the state quantity rank, and determine that the area having the mismatch is the abnormal area.

2. The oil mist concentration management apparatus according to claim 1, further comprising:
 an integrated quantity calculation unit configured to calculate integrated quantity of the coolant during operation of the machine based on the flow rate of the coolant detected by a flow meter; and
an average flow rate calculation unit configured to calculate an average flow rate of the coolant used by the machine based on the integrated quantity and a time period for which the machine is operated,
wherein the identifying unit uses the average flow rate of the coolant as the state quantity of the machine in each of the plurality of areas.

3. The oil mist concentration management apparatus according to claim 1, wherein, if there is an area where the state quantity rank is lower than the concentration rank, the rank comparison unit identifies that ventilation performance of the area is low.

4. The oil mist concentration management apparatus according to claim 1, further comprising a determination unit configured to determine whether the concentration of the oil mist acquired by the concentration acquisition unit is larger than a threshold value that is retained beforehand,
wherein if the determination unit determines that there is an area where the concentration of the oil mist is larger than the threshold value, the identifying unit identifies that the area is the abnormal area.

5. An oil mist management system comprising:
a machine provided in each of a plurality of areas;
a detection device provided in each of the plurality of areas, the detection device being configured to detect a state quantity regarding a running state of the machine;
a concentration measuring apparatus provided in each of the plurality of areas, the concentration measuring apparatus being configured to measure concentration of oil mist in each of the plurality of areas;
an oil mist concentration management apparatus configured to identify whether distribution of the oil mist in the plurality of areas is normal or abnormal on an area-by-area basis, based on the state quantity of the machine in each of the plurality of areas and the concentration of the oil mist in each of the plurality of areas; and
an output device configured to notify a user of an abnormal area which has been identified as abnormal by the oil mist concentration management apparatus,
wherein
the oil mist concentration management apparatus uses, as the state quantity regarding the running state of the machine, a flow rate of coolant used at time of operating the machine,
the oil mist concentration management apparatus includes
a concentration rank determination unit configured to determine a relative concentration rank regarding the concentration of the oil mist among the plurality of areas, based on the concentration of the oil mist in each of the plurality of areas,
a state quantity rank determination unit configured to determine a relative state quantity rank regarding the state quantity among the plurality of areas, based on the state quantity of the machine in each of the plurality of areas,
a rank comparison unit configured to compare the concentration rank and the state quantity rank to thereby extract an area having a match or a mismatch between the concentration rank and the state quantity rank, and determine that the area having the mismatch is the abnormal area.

6. An oil mist management method of managing oil mist in a factory having a machine in each of a plurality of areas, by an oil mist concentration management apparatus, the method comprising:
a state quantity acquisition step of acquiring a state quantity regarding a running state of the machine provided in each of the plurality of areas;
a measurement data acquisition step of acquiring concentration of oil mist measured in each of the plurality of areas;
a data processing step of identifying whether distribution of the oil mist in the plurality of areas is normal or abnormal on an area-by-area basis, based on the state quantity of the machine in each of the plurality of areas and the concentration of the oil mist in each of the plurality of areas; and
a notification step of notifying a user of an abnormal area which has been identified as abnormal in the data processing step,
wherein
as the state quantity regarding the running state of the machine, a flow rate of coolant used at time of operating the machine is used,
the data processing step includes
a concentration rank determination step that determines a relative concentration rank regarding the concentration of the oil mist among the plurality of areas, based on the concentration of the oil mist in each of the plurality of areas,
a state quantity rank determination step that determines a relative state quantity rank regarding the state quantity among the plurality of areas, based on the state quantity of the machine in each of the plurality of areas,
a rank comparison step that compares the concentration rank and the state quantity rank to thereby extract an area having a match or a mismatch between the concentration rank and the state quantity rank, and determine that the area having the mismatch is the abnormal area.

\* \* \* \* \*